United States Patent
Meyer

(12) 
(10) Patent No.: US 6,303,079 B1
(45) Date of Patent: Oct. 16, 2001

(54) CORROSION INHIBITOR COMPOSITIONS

(75) Inventor: George Richard Meyer, Missouri City, TX (US)

(73) Assignee: Nalco/Exxon Energy Chemicals, L.P., Sugar Land, TX (US)

(*) Notice: Subject to any disclaimer, the term of this patent is extended or adjusted under 35 U.S.C. 154(b) by 0 days.

(21) Appl. No.: 09/268,381

(22) Filed: Mar. 15, 1999

(51) Int. Cl.$^7$ .................................................. C23F 11/04
(52) U.S. Cl. ...................... 422/12; 106/14.12; 106/14.13; 106/14.15; 106/14.18; 106/14.27; 106/14.31; 148/243; 148/274; 208/47; 208/48; 252/390; 252/394; 422/7
(58) Field of Search ................................... 422/7, 12, 14; 252/390, 394; 148/243, 274; 208/48; 106/14.12, 14.13, 14.15, 14.18, 14.31, 14.27; 546/1, 268.1, 290

(56) References Cited

U.S. PATENT DOCUMENTS

| | | |
|---|---|---|
| 2,200,815 | 5/1940 | Ackley . |
| 2,995,520 | 8/1961 | Luvisi et al. . |
| 4,544,765 | 10/1985 | Patel . |
| 5,300,235 | 4/1994 | Clewlow et al. . |
| 5,322,640 | 6/1994 | Byrne et al. . |
| 5,993,693 | * 11/1999 | Meyer ................................. 252/390 |
| 6,171,521 | * 1/2001 | Meyer ................................. 252/394 |

OTHER PUBLICATIONS

"The Existence of Imidazoline Corrosion Inhibitors", Valone et al., Corrosion 84, No. 232, Apr. 2–6, 1984, pp. 232/1–8.

"Tall Oil Fatty Acid Anhydrides as Corrosion Inhibitor Intermediates", Corrosion 95, Fischer et al., No. 493, pp. 493/1–4.

"Mechanistsic Studies of the Corrosion Inhibitor Oleic Imidazoline", Edwards et al., Corrosion Science, vol. 36, No. 2, pp. 315–325, 1994.

"The Study of Inhibitors for Sour Gas Service", Suzuki et al., Corrosion Nace, pp. 384–389, Sep. 1981.

* cited by examiner

Primary Examiner—Krisanne Thornton
(74) Attorney, Agent, or Firm—K. L. Cummings; T. M. Breininger

(57) ABSTRACT

The present invention relates to a process for making and a method for using a corrosion inhibitor composition to reduce the corrosion rate of a metal by a fluid containing a corrosion agent. The corrosion inhibitor composition comprises at least a quaternized compound having an amido moiety. An example of the quaternized compound is a quaternized amido imidazoline.

17 Claims, No Drawings

CORROSION INHIBITOR COMPOSITIONS

FIELD OF THE INVENTION

The present invention relates to a process for producing and a method for using a corrosion inhibitor composition for reducing the corrosion rate of a metal by a fluid having at least one corrosion agent. More specifically, the invention relates to synthesis and use of one or more quaternized compounds having an amido moiety, for example quaternized imidazoline(s) having an amido moiety, in such a corrosion inhibitor composition used in oil and gas-field applications.

BACKGROUND OF THE INVENTION

In order to reduce the rate of corrosion of metals, and particularly metals containing iron, from one or more metal corrosion agents present in a fluid (i.e., a gas, liquid, slurry or a mixture thereof) a corrosion inhibitor is frequently introduced into the fluid to reduce the rate of corrosion of the metal vessel, pipeline and/or equipment used to store and transport the fluid. In oil and gas-field applications, for example, corrosion inhibitors are added to a wide array of systems, including without limitation, cooling systems, refinery units, pipelines, steam generators and oil or gas producing units in efforts to combat a variety of types of corrosion.

One example of corrosion, among others, typically encountered in the transport of a fluid containing one or more corrosion agents (hereinafter simply referred to as "fluid") is flow-induced corrosion. In the case of flow-induced corrosion, the degree of corrosion that occurs is presently believed to depend on a variety of factors, including the corrosiveness of the fluid itself, the metallurgy of the pipeline and the shear rate, temperature, and pressure of the fluid. Also, to the extent that a corrosion inhibitor is used, the inhibitor's ability to reduce the rate of corrosion of a metal from flow-induced corrosion, among other types of corrosion, is presently believed to depend on at least two factors. One factor is the inhibitor's chemical affinity for the metal surface. A second factor is the inhibitor's resistance to breakdown under high shear conditions. Therefore, it is currently believed that the rate of corrosion, especially flow-induced corrosion, of a metal more likely will be reduced where the inhibitor has good chemical affinity for the metal surface and can resist breakdown under high shear conditions. Many inhibitors have been developed to reduce corrosion. However, their activity is sufficiently low that higher concentrations are oftentimes required to effectively treat a pipeline, most particularly where flow-induced corrosion is a problem, thereby increasing operating costs.

Also, where a particular inhibitor shows good corrosion inhibition activity, it typically costs significantly more to manufacture than alternative inhibitors with lower activity. For example, quaternized imidazolines like those disclosed in U.S. Pat. No. 5,322,640 can be produced with, among other compounds, tall oil fatty acid (TOFA) and an alkyl polyamine, also often referred to as a polyalkylene polyamine, such as diethylenetriamine (DETA). It is well understood by those skilled in the art that the production of the amino imidazoline desired for synthesizing preferred imidazoline derivatives useful for corrosion inhibition is produced by reacting stoichiometric amounts (i.e., a 1:1 mole ratio) of a high molecular weight monocarboxylic fatty acid having from 16 to 32 carbon atoms with an alkyl polyamine (see e.g., U.S. Pat. Nos. 3,687,847 and 3,758,493). Often an excess amount of alkyl polyamine (for example, a TOFA:DETA mole ratio of about 0.77:1) has been used in previous commercial applications to produce the amino imidazoline.

The presence of a free amine moiety enhances the reactivity of the pendant alkyl amine group versus the unsubstituted nitrogen atom in the imidazoline ring. Various imidazoline derivatives are produced typically by reacting the imidazoline with organic carboxylic acids, such as, for example, acrylic acid ($CH_2CH_2COOH$), which preferably react with the imidazoline's pendant alkyl amine group, to enhance the its corrosion inhibition activity by increasing its partitioning into water.

Conventionally, the 1:1 TOFA:DETA mole ratio has been considered desirable because it was heretofore thought to yield a substituted imidazoline with a pendant alkyl amine group that has at least one free amine (e.g., a $NH_2$ group) available for interaction with a metal surface. However, the Applicant has discovered that, unexpectedly and surprisingly, the reaction product produced with such low TOFA:DETA ratios (i.e., from about 0.6:1 to about 1.2:1) can produce a reaction product mixture comprising both an amino imidazoline and an amido imidazoline, although the amido imidazoline is believed to be produced at a lower mole% than the amino imidazoline. Heretofore, it was believed by those skilled in the art that the only imidazoline formed would be an amino imidazoline in the reaction product where a low TOFA:DETA mole ratio was used in the synthesis process. Moreover, it was believed that using higher TOFA:DETA mole ratios, in the range of from about 1.3:1 to about 500:1, would lead to the production of excess amounts of amido type imidazolines. Conventionally, such amido imidazolines and their derivatives generally were considered to have little to no corrosion inhibition activity or potentially to have detrimental effects on the reaction product's corrosion inhibition activity. Put another way, amido type imidazolines were considered an impurity or contaminant in the reaction product because they lacked a pendant group with a heteroatom (e.g., nitrogen, sulfur or oxygen) having a pair of nonbonding electrons freely available for interaction with a metal surface.

Accordingly, until the disclosure of the present invention, those skilled in the art of synthesizing corrosion inhibitors refrained from reacting higher mole ratios of a monocarboxylic acid (e.g., TOFA) with an alkyl polyamine (e.g., DETA) and/or producing imidazoline derivatives where the group pendant to the imidazoline ring contains an amido moiety, generally described as —N—(C=O)—R. In this instance, the pair of nonbonding electrons on the nitrogen atom of the pendant group would have a preferential affinity for the proximate carbonyl moiety over that for the metal surface. In turn, it was thought that this absence of a freely available pair of nonbonding electrons would reduce the compound's ability to interact with a metal surface, and thereby reduce its overall inhibition activity.

The cost of alkyl polyamines, such as DETA, is high (e.g., $1.50/lb.) as compared with a monocarboxylic fatty acid, such as TOFA (e.g., 24¢/lb.). Consequently, the use of certain imidazolines for reducing the corrosion rate of a metal, most particularly for improving its resistance to flow-induced corrosion, can lead to increased operating costs. A comparatively lower cost inhibitor is desired that has corrosion inhibition performance comparable to or better than inhibitors presently used for treating systems experiencing flow-induced corrosion, among other metal corrosion problems.

A substantial number of corrosion inhibitors have been disclosed for reducing the rate of corrosion of metal-containing storage and transport systems. More specifically, a number of corrosion inhibitors have been disclosed most particularly for treating flow-induced corrosion, including, among others, quaternized imidazolines. However, these imidazolines are relatively costly to manufacture. Accordingly, a need exists for a corrosion inhibitor that is less costly to manufacture compared to such known inhibitors.

SUMMARY OF THE INVENTION

According to one aspect of the present invention, there is provided a method of using a corrosion inhibitor composition for reducing the corrosion rate of a metal by a fluid having at least one corrosion agent, said method comprising: (a) introducing said corrosion inhibitor composition into said fluid, said inhibitor composition having at least a first compound, A, and a second compound, B, wherein the A:B mole ratio is in a range of from about 1.1:1 to about 1000:1, wherein (i) A is a quaternized compound having the general formula:

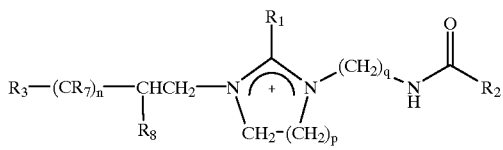

A wherein, $R_1$ and $R_2$ are each independently a moiety selected from the group consisting of: (i) substituted and unsubstituted, saturated and unsaturated alkyl groups having from about 5 to about 29 carbon atoms; (ii) substituted and unsubstituted, saturated and unsaturated alkyl groups having from about 5 to about 29 carbon atoms, wherein said alkyl group is at least oxygenized, sulfurized or phosphorylized; and (iii) combinations thereof; $R_3$ is a moiety selected from the group consisting of $—CO_2H$, $—SO_3H$, $—PO_3H_2$, $—CO_2R_7$, $—CONH_2$, $—CONHR_7$ and $—CON(R_7)_2$ groups and combinations thereof; each $R_7$ is independently selected from the group consisting of hydrogen and linear and branched alkyl, aryl, alkylaryl, cycloalkyl and heteroaromatic groups having from 1 to about 10 carbon atoms, and combinations thereof; $R_8$ is hydrogen or a linear alkyl group having from 1 to about 10 carbon atoms; and n=0 to about 8, p=1 to about 5 and q=2 to about 10; and B is a quaternized compound having the general formula:

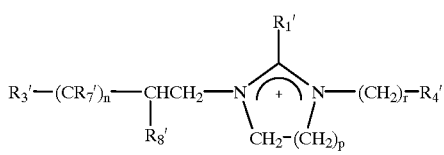

B wherein, $R_1'$ is a moiety selected from the group consisting of: (i) substituted and unsubstituted, saturated and unsaturated alkyl groups having from about 5 to about 29 carbon atoms; (ii) substituted and unsubstituted, saturated and unsaturated alkyl groups having from about 5 to about 29 carbon atoms, wherein said alkyl group is at least oxygenized, sulfurized or phosphorylized; and (iii) combinations thereof; $R_4'$ is a moiety selected from the group consisting of polyalkylene polyamines, alcohol and thiol groups having from about 2 to about 16 carbon atoms, and combinations thereof; $R_3'$ is a moiety selected from the group consisting of $—CO_2H$, $—SO_3H$, $—PO_3H_2$, $—CO_2R_7'$, $—CONH_2$, $—CONHR_7'$ and $—CON(R_7')_2$ groups and combinations thereof; each $R_7'$ is independently selected from the group consisting of hydrogen and linear and branched alkyl, aryl, alkylaryl, cycloalkyl and heteroaromatic groups having from 1 to about 10 carbon atoms, and combinations thereof; $R_8'$ is hydrogen or a linear alkyl group having from 1 to about 10 carbon atoms; and n=0 to about 8, p=1 to about 5 and r=0 to about 10; and (b) contacting said metal with the fluid of step (a).

According to another aspect of the present invention, there is provided a method for using a corrosion inhibitor composition for reducing the corrosion rate of a metal by a fluid having at least one corrosion agent, and method comprising: (a) introducing said corrosion inhibitor composition into said fluid, said inhibitor composition having at least a first compound, A, as defined above, and being substantially free of a second compound, B, as defined above, and (b) contacting said metal with the fluid of step (a).

According to a further aspect of the present invention, there is provided a process for producing a composition comprising at least a quaternized compound having an amido moiety, comprising the steps of: (a) selecting a first organic compound from the group consisting of: (i) substituted and unsubstituted, saturated and unsaturated fatty acids having from about 6 to about 30 carbon atoms; (ii) substituted and unsubstituted, saturated and unsaturated fatty acids having from about 6 to about 30 carbon atoms, wherein said fatty acid is at least oxygenized, sulfurized or phosphorylized; and (iii) combinations thereof; (b) selecting an alkyl polyamine from the group having the general formula:

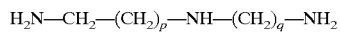

wherein p=1 to about 5 and q=2 to about 10; (c) selecting a second organic compound from the group consisting of (i) substituted and unsubstituted, α,β-unsaturated carboxylic fatty acids, and amide and ester derivatives thereof, having from about 3 to about 11 carbon atoms; (ii) substituted and unsubstituted, α,β-unsaturated sulfonic and phosphonic fatty acids having from about 2 to about 11 carbon atoms; and (iii) combinations thereof; (d) mixing said first organic compound and said alkyl polyamine in a mole ratio in a range of from about 1.1:1 to about 500:1 to produce at least one intermediate compound, wherein said mole ratio is the total moles of said first organic compound to the total moles of said alkyl polyamine; and (e) mixing said at least one intermediate compound with said second organic compound to produce said composition.

DESCRIPTION OF THE INVENTION

As discussed above, the production of certain imidazoline inhibitors can be relatively costly compared to other known inhibitors. Accordingly, one aspect of the invention, discussed below, relates to a method for synthesizing quaternized imidazolines as well as other related quaternized compounds described by the following general formula, hereinafter referred to as compound A:

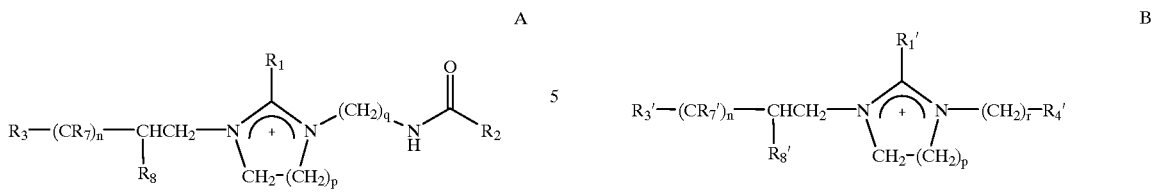

where $R_1$ and $R_2$ are each independently a moiety selected from the group consisting of (i) substituted and unsubstituted, saturated and unsaturated alkyl groups having from about 5 to about 29 carbon atoms; (ii) substituted and unsubstituted, saturated and unsaturated alkyl groups having from about 5 to about 29 carbon atoms, wherein said alkyl group is at least oxygenized, sulfurized or phosphorylized; and (iii) combinations thereof; $R_3$ is a moiety selected from the group consisting of —$CO_2H$, —$SO_3H$, —$PO_3H_2$, —$CO_2R_7$, —$CONH_2$, —$CONHR_7$ and —$CON(R_7)_2$ groups and combinations thereof; each $R_7$ is independently selected from the group consisting of hydrogen and linear and branched alkyl, aryl, alkylaryl, cycloalkyl and heteroaromatic groups having from 1 to about 10 carbon atoms, and combinations thereof; $R_8$ is hydrogen or a linear alkyl group having from 1 to about 10 carbon atoms; and n=0 to about 8, p=1 to about 5 and q=2 to about 10. It is to be understood that the range of carbon atoms specified for each group described herein refers to the main chain of the alkyl groups, and does not include carbon atoms that may be contributed by substituents.

Many quaternary ammonium compounds are acyclic, having the general formula $R_4N^+X^-$, and are a type of ionic organic compound with at least one nitrogen atom. However, heterocyclic compounds with at least one nitrogen atom also can be quaternary ammonium compounds.

In the case of acyclic quaternary ammonium compounds, a nitrogen is covalently bonded to four organic groups and bears a localized positive charge that is balanced by a negative counterion. The negative counterion may be either attached to or unattached to, but still associated with, the rest of the compound.

In the case of heterocyclic ammonium compounds, at least one nitrogen has four bonds, which are either (a) each single bonds or (b) two single bonds and a double bond. The present invention produces heterocyclic quaternized ammonium compounds, which, for convenience, are depicted as having two single bonds and a double bond with the double bond shown as a resonance type structure, indicating that it is delocalized between two nitrogen atoms of the same heterocyclic ring. However, it will be understood by those skilled in the art that the specified groups pendant to each nitrogen, could also, in whole or in part, be pendant to a single nitrogen.

The quaternized compounds A may be used alone or in combination with other corrosion inhibitors and/or corrosion inhibitor formulation substances, including, without limitation, solvents, surfactants, and quaternized salts, which are more fully described below. Preferably, however, the above-described quaternized compounds A are used at least in combination with a quaternized compound B described by the following general formula:

where $R_1'$ is a moiety selected from the group consisting of (i) substituted and unsubstituted, saturated and unsaturated alkyl groups having from about 5 to about 29 carbon atoms; (ii) substituted and unsubstituted, saturated and unsaturated alkyl groups having from about 5 to about 29 carbon atoms, wherein said alkyl group is at least oxygenized, sulfurized or phosphorylized; and (iii) combinations thereof; $R_4'$ is a moiety selected from the group consisting of polyalkylene polyamines, alcohol and thiol groups having from about 2 to about 16 carbon atoms, and (iii) combinations thereof; $R_3'$ is a moiety selected from the group consisting of —$CO_2H$, —$SO_3H$, —$PO_3H_2$, —$CO_2R_7'$, —$CONH_2$, —$CONHR_7$ and —$CON(R_7')_2$ groups and combinations thereof; each $R_7'$ is independently selected from the group consisting of hydrogen and linear and branched alkyl, aryl, alkylaryl, cycloalkyl and heteroaromatic groups having from 1 to about 10 carbon atoms, and combinations thereof; $R_8'$ is hydrogen or a linear alkyl group having from 1 to about 10 carbon atoms; and n=0 to about 8, p=1 to about 5 and r=0 to about 10. It is to be understood that the range of carbon atoms specified for each group described herein refers to the main chain of the alkyl groups, and does not include carbon atoms that may be contributed by substituents.

All derivatives of compounds A and B have heterocyclic rings containing two nitrogen atoms. The heterocyclic rings of structures A and B preferably have from about 3 to 7 carbon atoms, more preferably from about 3 to 5 carbon atoms and most preferably 3 carbon atoms. Compounds A and B are quaternized imidazolines when there are 3 carbon atoms, quaternized tetrahydropyrimidines when there are 4 carbon atoms, and so on.

As specified above. the derivative of compound A may have one group pendant to the first nitrogen atom of the heterocyclic ring containing a —$CO_2H$, —$SO_3H$, —$PO_3H_2$, —$CO_2R_7$, —$CONH_2$, —$CONHR_7$ and —$CON(R_7)_2$ group and a second group pendant to the second nitrogen atom of the heterocyclic ring containing an amido group.

Also, the derivative of compound A may have a group pendant to the apex carbon bridging the first and second nitrogen of the heterocyclic ring that is (i) a substituted or unsubstituted, saturated or unsaturated alkyl group having from about 5 to about 29 carbon atoms; (ii) a substituted or unsubstituted, saturated or unsaturated, oxygenized, sulfurized or phosphorylized alkyl group having from about 5 to about 29 carbon atoms; or (iii) a combination thereof. Generally, preferred $R_1$ moieties include (a) unsubstituted, unsaturated alkyl groups having from about 7 to about 23 carbon atoms, (b) substituted, unsaturated alkyl groups having from about 7 to about 23 carbon atoms, and (c) sulfurized unsubstituted, saturated or unsaturated alkyl groups having from about 7 to about 23 carbon atoms. More preferred $R_1$ moieties include (a) unsubstituted, unsaturated alkyl groups having from 11 to about 23 carbon atoms, and (b) substituted, unsaturated alkyl groups having from about 11 to about 23 carbon atoms. Most preferred $R_1$ moieties include unsubstituted, unsaturated alkyl groups having from about 17 to about 21 carbon atoms.

Examples of suitable substituents include, without limitation, OH, SH, halogen atoms, alkyl, aryl, alkylaryl and heteroaromatic groups and, combinations thereof.

The group pendant to the first nitrogen atom of the heterocyclic ring has at least 2 carbon atoms, one of which may be substituted with a linear alkyl group having from 1 to about 10 carbon atoms. The pendant group may or may not have a conjugated portion with up to 8 carbon atoms which may or may not be substituted with a linear or branched alkyl, aryl, alkylaryl, cycloalkyl or heteroaromatic group having from 1 to about 10 carbon atoms, or a combination thereof.

The group pendant to the first nitrogen atom of the heterocyclic ring also contains a $-CO_2H$, $-SO_3H$, $-PO_3H_2$, $-CO_2R_7$, $-CONH_2$, $-CONHR_7$ or $-CON(R_7)_2$ moiety. Preferably, the group pendant to the first nitrogen atom of the heterocyclic ring contains a carboxylate, sulfonate or phosphonate moiety, more preferably contains a carboxylate or sulfonate moiety and most preferably contains a carboxylate moiety.

The group pendant to the second nitrogen atom of the heterocyclic ring contains an amido moiety. Preferably, the group pendant to the second nitrogen atom of the heterocyclic ring contains a linear or branched alkyl group having from 2 to about 10 carbon atoms, more preferably contains a linear or branched alkyl group having from about 2 to about 6 carbon atoms and most preferably contains a linear alkyl group having from about 2 to about 4 carbon atoms.

$R_2$ of the amido moiety is (i) a substituted or unsubstituted, saturated or unsaturated alkyl group having from about 5 to about 29 carbon atoms; (ii) a substituted or unsubstituted, saturated or unsaturated, oxygenized, sulfurized or phosphorylized alkyl group having from about 5 to about 29 carbon atoms; or (iii) a combination thereof. Generally, preferred $R_2$ moieties include (a) unsubstituted, unsaturated alkyl groups having from about 7 to about 23 carbon atoms, (b) substituted, unsaturated alkyl groups having from about 7 to about 23 carbon atoms, and (c) sulfurized unsubstituted, saturated or unsaturated alkyl groups having from 7 to about 23 carbon atoms. More preferred $R_2$ moieties include (a) unsubstituted, unsaturated alkyl groups having from about 11 to about 23 carbon atoms, and (b) substituted, unsaturated alkyl groups having from about 11 to about 23 carbon atoms. Most preferred $R_2$ moieties include unsubstituted, unsaturated alkyl groups having from about 17 to about 21 carbon atoms.

Examples of suitable substituents include, without limitation, OH, SH, halogen atoms, alkyl, aryl, alkylaryl and heteroaromatic groups and, combinations thereof.

For example, one of the most preferred derivatives of compound A is a quaternized amido imidazoline having the following formula, hereinafter referred to as compound $A_1$:

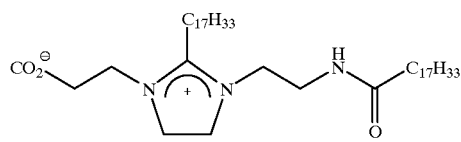

where $R_1$ and $R_2$ are $C_{17}H_{33}$, $R_3$ is $COO^-$, $R_8$ is hydrogen and n=0, p=1 and q=2 in formula A.

The synthesis of compound A derivatives, and more specifically, of the illustrative compound, $A_1$, described above is discussed more fully below. However, it should be understood that commercial manufacture of compounds A or B will typically lead to a mixture of final products resulting from an incomplete cyclization step and competing reaction pathways that can yield compounds A and/or B. Accordingly, a mixture of compounds includes at least a compound A derivative in combination with other compounds, including, without limitation, some unreacted starting material, some intermediate mono-, di- and/or polyamides arising from the reaction pathway for compound A derivatives and possibly other derivatives produced by competing reaction pathways, such as, a compound B derivative and/or its intermediate mono-, di- and/or polyamides.

In a most preferred embodiment of the invention, a compound A derivative is used in combination with a compound B derivative. The preferred mole ratio of a compound A to a compound B is in the range of from about 1.1:1 to about 100:1, but may go as high as about 1000:1. However, at increasingly higher mole ratios of compound A to compound B, the cost of producing such a combination may not justify the incremental improvement in inhibition performance. Therefore, the more preferred mole ratio of compound A to compound B is in the range of from about 1.1:1 to about 25:1 and the most preferred mole ratio of compound A to compound B is in the range of from about 2:1 to about 10:1.

Preferred derivatives of compound B for use as a corrosion inhibitor in combination with derivatives of compound A have the following general formula:

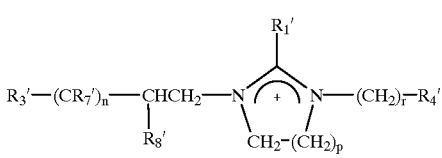

where $R_1'$ is a moiety selected from the group consisting of (i) substituted and unsubstituted, saturated and unsaturated alkyl groups having from about 5 to about 29 carbon atoms; (ii) substituted and unsubstituted, saturated and unsaturated alkyl groups having from about 5 to about 29 carbon atoms, wherein said alkyl group is at least oxygenized, sulfurized or phosphorylized; and (iii) combinations thereof; $R_4'$ is a moiety selected from the group consisting of polyalkylene polyamines, alcohol and thiol groups having from about 2 to about 16 carbon atoms, and combinations thereof; $R_3'$ is a moiety selected from the group consisting of $-CO_2H$, $-SO_3H$, $-PO3H_2$, $-CO_2R_7'$, $-CONH_2$, $-CONHR_7'$ and $-CON(R_7')_2$ groups and combinations thereof; each $R_7'$ is independently selected from the group consisting of hydrogen and linear and branched alkyl, aryl, alkylaryl, cycloalkyl and heteroaromatic groups having from 1 to about 10 carbon atoms, and combinations thereof; $R_8'$ is hydrogen or a linear alkyl group having from 1 to about 10 carbon atoms; and n=0 to about 8, p=1 to about 5 and r=0 to about 10.

Generally, preferred $R_1'$ moieties include (a) unsubstituted, unsaturated alkyl groups having from about 7 to about 23 carbon atoms, (b) substituted, unsaturated alkyl groups having from about 7 to about 23 carbon atoms, and (c) sulfurized unsubstituted, saturated or unsaturated alkyl groups having from about 7 to about 23 carbon atoms. More preferred $R_1'$ moieties include (a) unsubstituted, unsaturated alkyl groups having from about 11 to about 23 carbon atoms, and (b) substituted, unsaturated alkyl groups having from about 11 to about 23 carbon atoms. Most preferred $R_1'$ moieties include unsubstituted, unsaturated alkyl groups having from about 17 to about 21 carbon atoms.

Examples of suitable substituents include, without limitation, OH, SH, halogen atoms, alkyl, aryl, alkylaryl and heteroaromatic groups, and combinations thereof.

Preferred $R_4'$ moieties for compound B derivatives have the following general formula:

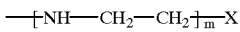

$$-[NH-CH_2-CH_2]_m-X$$

where X is selected from the group consisting of $NH_2$, $NHR_6$, $N(R_6)_2$, OH and SH, and combinations thereof, each $R_6$ is independently a linear alkyl group or branched alkyl group having from 1 to about 8 carbon atoms and m=0 to about 5. In more preferred $R_4'$ moieties, m=0 to about 3 and X is selected from the group consisting of $NH_2$ and OH. In the most preferred $R_4'$ moieties, m=0 to about 2 and X is $NH_2$.

Preferably $R_3'$ moieties for compound B include carboxylate, sulfonate and phosphonate groups. More preferred $R_3'$ moieties for compound B derivatives include carboxylate and sulfonate groups and the most preferred moiety is a carboxylate group.

Also, more preferred compound B derivatives have n=0 to about 6, p=1 to about 3 and r=1 to about 6, while most preferred compound B derivatives have n=0 to about 4, p=1 and q=about 2 to about 4.

Accordingly, one of the most preferred compound B derivatives has the following formula:

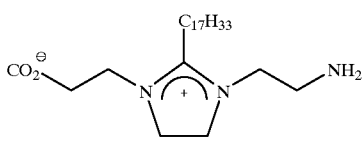

$B_1$ where $R_1'$ is $C_{17}H_{33}$, $R_4'$ is $NH_2$, $R_3'$ is $COO^-$, $R_8'$ is hydrogen and n=0, p=1 and r=2 in formula B.

Therefore, for example, one of the most preferred mixtures of corrosion inhibitors produced in accordance with the synthesis description below is believed to be a mixed reaction product having at least compound $A_1$ and compound $B_1$ in a mole ratio of about 5:1.

The quaternized compounds having an amido moiety can be made using a wide array of organic acids and acid derivatives and alkyl polyamines. Generally, two different types of organic compounds can be used to practice the invention.

The first type of organic compound is generally selected from the class of fatty acids. More specifically, the fatty acids useful for practicing the invention can be selected from the group consisting of substituted and unsubstituted, saturated and unsaturated fatty acids having from about 6 to about 30 carbon atoms; substituted and unsubstituted, saturated and unsaturated fatty acids having from about 6 to about 30 carbon atoms, wherein the fatty acid is at least oxygenized, sulfurized or phosphorylized; and combinations thereof. It is to be understood that the range of carbon atoms specified for each group described herein refers to the main chain of the acid, and does not include carbon atoms that may be contributed by substituents.

Generally, preferred fatty acids of the first type include (a) unsubstituted, unsaturated fatty acids having from about 8 to about 24 carbon atoms, (b) substituted, unsaturated fatty acids having from about 8 to about 24 carbon atoms and (c) sulfurized unsubstituted, saturated or unsaturated fatty acids having from about 8 to about 24 carbon atoms. More preferred fatty acids of the first type include (a) unsubstituted, unsaturated fatty acids having from about 12 to about 24 carbon atoms and (b) substituted, unsaturated fatty acids having from about 12 to about 24 carbon atoms. Most preferred fatty acids of the first type include unsubstituted, unsaturated fatty acids having from about 18 to about 22 carbon atoms.

The second type of organic compound is generally selected from the class of α,β-unsaturated fatty carboxylic acids and amide and ester derivatives thereof, α,β-unsaturated fatty sulfonic or phosphonic acids, and combinations thereof. More specifically, the second type of organic material useful for practicing the invention can be selected from the group consisting of (i) substituted and unsubstituted, α,β-unsaturated carboxylic fatty acids and amide and ester derivatives thereof having from about 3 to about 11 carbon atoms; (ii) substituted or unsubstituted, α,β-unsaturated sulfonic and phosphonic fatty acids having from about 2 to about 11 carbon atoms; and (iii) combinations thereof. It is to be understood that the range of carbon atoms specified for each group described herein refers to the main chain of the acid, and does not include carbon atoms that may be contributed by substituents.

Generally, preferred α,β-unsaturated carboxylic fatty acids and amide and ester derivatives thereof, and α,β-unsaturated sulfonic and phosphonic fatty acids are (a) unsubstituted and have from about 2 to about 9 carbon atoms, and (b) substituted and have from about 2 to about 9 carbon atoms. More preferred α,β-unsaturated carboxylic fatty acids and amide and ester derivatives thereof, and α,β-unsaturated sulfonic and phosphonic fatty acids are (a) unsubstituted and have from about 2 to about 7 carbon atoms, and (b) substituted and have from about 2 to about 7 carbon atoms. Most preferred α,β-unsaturated carboxylic fatty acids and amide and ester derivatives thereof, α,β-unsaturated sulfonic and phosphonic fatty acids are unsubstituted and have from about 2 to about 5 carbon atoms.

Examples of suitable substituents include, without limitation, alkyl, aryl, alkylaryl, cycloalkyl and heteroaromatic groups, and combinations thereof.

Generally, preferred types of acid groups for selecting α,β-unsaturated fatty acids are carboxylic and sulfonic acids, while the most preferred acid group is carboxylic acid.

The alkyl polyamine(s) that can be used to practice the invention can be selected from the group having the following general formula:

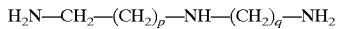

$$H_2N-CH_2-(CH_2)_p-NH-(CH_2)_q-NH_2$$

wherein p=1 to about 5 and q=2 to about 10.

Generally, preferred alkyl polyamines include those where p=1 to 2 and q=2 to 3. More preferred alkyl polyamines include p=1 and q=2 to 3. Most preferred alkyl polyamines include those where p=1 and q=2.

To produce a composition comprising an amide intermediate for a quaternized compound having an amido moiety, the mole ratio of the first organic acid to the alkyl polyamine may be selected from the range of from about 1.1:1 to about 500:1, hereinafter referred to as the amido mole ratio range. As used herein, amido mole ratio means the ratio of the total number of moles of the first organic acid to the total number of moles of alkyl polyamine used in a process for making an amide intermediate for a quaternized compound having an amido moiety. Generally, the preferred amido mole ratio range of the first organic acid to the alkyl polyamine is selected from the range of about from 1.3:1 to about 100:1. The more preferred amido mole ratio range of the first organic compound to the alkyl polyamine is selected from the range of about from 1.3:1 to about 10:1. The most preferred amido mole ratio range of the first organic compound to the alkyl polyamine is selected from the range of from about 1.3:1 to about 5:1.

It should be understood that the terms "mix", "mixed" or "mixing" as used herein are intended to embrace all synthesis procedures, including, without limitation, batch, continuous, in-situ, interfacial and/or solution type processes and combinations thereof. Moreover, such terms and reference to any intermediates produced are used for convenience and for clarifying the scope of the Applicant's invention. Accordingly, such terms should not be construed to limit the claimed invention to: (a) any particular sequence of reaction steps suggested herein, or (b) the production and/or separation of any specified amount of intermediate(s) for any specified length of time as a prerequisite to a subsequent process step.

The amide imidazoline intermediate mixture produced from the first organic compound and the alkyl polyamine is mixed with an organic compound of the second type to produce a quaternized compound having an amido moiety.

To produce a quaternized compound having a moiety containing a hydrocarbon and carbonyl, sulfonyl or phosphonyl group, the amide intermediate mixture is mixed with one or more of the α,β-unsaturated fatty acids or acid derivatives, described above as the second organic compound. Preferably, the relative amounts of the amide imidazoline mixture and the second organic acid or acid derivative are determined on a mole ratio basis. As mentioned above, the intermediate mixtures produced in the process of this invention can comprise other compounds in addition to the target intermediate species (e.g., amide imidazoline intermediate species) specified for a particular process.

Thus, a composite molecular weight can be used to calculate the number of moles of a particular intermediate mixture. Theoretically, such a composite molecular weight determination could represent the molecular weights of all chemical species of the mixture and their respective mole percent contributions to the mixture composition. However, making such a determination requires time-consuming and tedious analysis of the mixture composition. Consequently, for convenience, the composite molecular weight for an intermediate mixture, produced by the processes of the present invention, was determined herein by presuming the mixture is primarily comprised of the target species. So, for example, the composite molecular weight assigned to the amide imidazoline mixture of the Example below is 613 grams/mole (i.e., the molecular weight of the target imidazoline). Accordingly, such composite molecular weights can be used to calculate the number of moles of the mixture, and thereby determine the preferred amount of the second organic compound to be used in view of the mole ratio ranges specified below.

For a quaternized compound having an amido moiety, the mole ratio of the target amide intermediate mixture to the second organic acid or acid derivative is preferably selected from the range of from about 1:1 to about 1:2.5. More preferably, the mole ratio of the target amide intermediate mixture to the second organic acid or acid derivative is selected from the range of from about 1:1 to about 1:2. Most preferably, the mole ratio of the target amide intermediate mixture to the second organic acid or acid derivative is selected from the range of from about 1:1 to about 1: 1.5.

The corrosion inhibitors of the present invention can be used in any system exposed to fluids (i.e., liquid, gas, slurry or mixture thereof) containing a metal corrosion agent where improved corrosion inhibition is desired. However, the corrosion inhibitors of the present invention are particularly well-suited for use in oil and gas field applications and refinery operations.

With respect to such oil and gas field applications, the corrosion inhibitors of the present invention may be added to oil and/or gas fluids in the form of a solution or dispersion in water or an organic solvent. Examples of suitable solvents are alcohols such as methanol, ethanol, isopropanol, isobutanol, secondary butanol, glycols, and aliphatic and aromatic hydrocarbons.

The amount of active ingredient in a corrosion inhibitor formulation required to sufficiently reduce the rate of corrosion varies with the system in which it is used. Methods for monitoring the severity of corrosion in different systems are well-known to those skilled in the art, and may be used to decide the effective amount of active ingredient required in a particular situation. The compounds may be used to impart the property of corrosion inhibition to a composition for use in an oil or gas field application and may have one or more functions other than corrosion inhibition, e.g. scale inhibition.

The inhibitors of the type described herein have proven to be particularly effective for inhibiting corrosion of mild steel in hydrocarbon, oil/brine mixtures and aqueous systems under a variety of conditions. The inhibitor compositions claimed herein are preferably used in sweet systems, i.e., systems having a relatively high $CO_2$ concentration. However, use of such compositions in systems having sour conditions (i.e., systems having a relatively high $H_2S$ concentration) is also acceptable. Although fluid content of flow lines may vary, the inhibitor may be used in a variety of environments. Oil cuts in the field can range from less than 1% (oil field) to 100% (refinery) oil, while the nature of the water can range from 0 to 300,000 ppm TDS (total dissolved solids). In addition, the inhibitor compositions of the present invention would also be useful in large diameter flow lines of from about 1 inch to about 4 feet in diameter, small gathering lines, small flow lines and headers. In a preferred method, the inhibitor composition is added at a point in the flow line upstream from the point at which corrosion prevention is desired.

In practice, the inhibitor compositions of the present invention are preferably added to the flow line continuously to maintain a corrosion inhibiting dose of from about 0.01 to about 5000 ppm. More preferably, the corrosion inhibiting dose is from about 0.1 to about 500 ppm. In a most preferred embodiment of the present invention, the corrosion inhibiting dose is from about 1 to about 250 ppm. Although a most preferred use of the corrosion inhibitor compositions of the present invention is for mild steel flow lines, it is believed that the inhibitor compositions are also effective in inhibiting corrosion in other types of metallurgy. In certain cases, batch treatments are the method of choice for application of the inhibitor compositions of the present invention. However, the invention can also be practiced using a continuous process. Dosage rates for batch treatments range from about 0.1 to about 50,000 ppm. In a preferred embodiment of the present invention, the flow rate of the flow line in which the inhibitor composition is used is between 0 and 100 feet per second. A more preferred flow rate is between 0.1 and 50 feet per second. In some cases. the inhibitors of the present invention may be formulated with water in order to facilitate addition to the flow line.

The inhibitors of the present invention may be used alone or in combination with other compounds. Typical formulations include pour point depressants and/or surfactants. Examples of suitable pour point depressants are $C_1$ to $C_3$ linear or branched alcohols, ethylene and propylene glycol. Examples of suitable surfactants are ethoxylated nonylphenols and/or ethoxylated amines as wetting agents or additives for dispersing the inhibitor into the fluid stream to which they are added. The surfactant is advantageously water soluble to allow the product to better wet the surface of the flow line where corrosion may take place. Water soluble surfactants utilized may be non-ionic, cationic or anionic and will generally have a hydrophilic-lipophilic (HLB) value of about 1. Oil soluble surfactants may be utilized if it is desired to disperse the inhibitor composition into a hydrocarbon fluid. Oil soluble surfactants may be non-ionic, cationic or anionic. These surfactants typically have an HLB value less than 7.

Other compounds which may also be blended with the inhibitor compositions claimed herein are quaternary amines, such as fatty, cyclic or aromatic amines quaternized with lower alkyl halides or benzyl chloride and certain amides. In addition, formulations including the inhibitors of the present invention may include filming agents such as p-toluenesulfonic acid and dodecylbenzenesulfonic acid. The corrosion inhibitor may also contain components which are typically included in corrosion inhibiting compositions, such as scale inhibitors and/or surfactants. In some instances, it may be desirable to include a biocide in the composition.

An example of a formulation which has been generally found to give superior performance is presented in Table I.

TABLE I

| Component | % by weight |
|---|---|
| Water | 10–60 |
| Methanol | 5–30 |
| Isopropanol | 5–30 |
| p-Toluenesulfonic acid | 0–5 |
| Ethoxylated alkyl amine surfactant | 2–15 |
| Quaternized compound of the present invention | 5–50 |
| Quaternary salt | 0–15 |

An example of a quaternary salt is an alkyl pyridine benzyl chloride quaternary salt. In the alkyl pyridine benzyl chloride quaternary salt, the alkyl group is preferably a methyl, ethyl or disubstituted alkyl group. The ethoxylated alkyl amine surfactant preferably has a carbon chain length of from about $C_{10}$ to about $C_{30}$ and preferably has about 20 moles of ethylene oxide per mole of amine.

The formulation is preferably produced by blending several ingredients into a homogeneous mixture. Though not critical to practicing the invention, the preferred order of addition is as follows: i) quaternized compound, ii) methanol and/or isopropanol, iii) quaternary salt, iv) ethoxylated alkyl amine surfactant, v) water and vi) p-toluenesulfonic acid.

The resultant inhibitor formulation may be used in a variety of petroleum operations in the oil and gas industry. It can be used to treat systems used in primary, secondary and tertiary oil and gas recovery. The inhibitor formulation may be introduced to such systems in accordance with techniques well-known to those skilled in the art. For example, one technique in which the inhibitor formulation can be used is the squeeze treating technique, whereby the inhibitor formulation is injected under pressure into a producing formation, adsorbed onto the strata and absorbed as the fluids are produced. The inhibitor formulation can further be added in water flooding operations of secondary oil recovery, as well as be added to pipelines, transmission lines and refinery units. The inhibitor formulation may also be used to inhibit acid solution in well-acidizing operations.

The following non-limiting example of a preferred compound that may be made and used as claimed herein is provided for illustrative purposes only.

Also, it will be apparent to those skilled in the art, that the reaction schematics specifying particular intermediates and final products illustrate only those compounds which the Applicant presumes are significant compounds formed based on current principles of organic reaction chemistry and qualitative infrared analysis of the final reaction product. Illustration of a specified intermediate does not exclude the presence of other significant intermediate(s) important to the formation of the final product. Also, illustration of a final compound does not exclude the presence of other compounds in the final composition, including, without limitation, the unreacted starting reactants, intermediates and other final compound(s), if any, produced by competing reaction pathways.

EXAMPLE

Synthesis of a Quaternized Amido Imidazoline

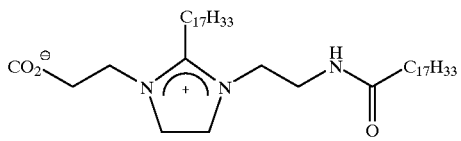

Preparation of Amide Imidazoline Mixture 175 g (0.62 mol) of tall oil fatty acid mixture (TOFA, comprised of about 46% oleic acid, about 41% linoleic acid, about 4% stearic acid and about 9% other acids) was placed in a 500 mL round bottom four-neck flask equipped with an overhead stirrer, addition funnel, thermocouple and Dean-Stark trap. The acid was heated to 60° C. and a sweep of nitrogen gas was maintained over the surface of the liquid throughout the reaction. When the temperature reached 60° C., 35 g (0.34 mol) of diethylenetriamine (DETA) was added dropwise rapidly. An exotherm of about 40° C. was observed. The mixture was heated to 175° C. with stirring until the theoretical amount of water for amide formation (11 g) was collected. The infrared spectrum of the mixture at this point indicated the presence of amide (absorption at about 1630 and 1550 $cm^{-1}$) and free N-H (absorption at about 3315 $cm^{-1}$). The temperature was increased to 225° C. and maintained there for 2 hours (84% of the theoretical amount of water for 100% imidazoline formation was collected). The infrared spectrum exhibited the same two broad bands noted above and a sharper, intense band between them around 1610 $cm^{-1}$, indicative of imidazoline.

Reaction of Amide Imidazoline Mixture with Acrylic Acid 61.3 g (0.1 mol, presuming the composite molecular weight of the amide imidazoline is 613 g/mole) of the resultant amide imidazoline mixture was weighed into a 250 mL round bottom four-neck flask equipped with an overhead stirrer, addition funnel and thermocouple. To this was added 8.6 g (0.12 mol) acrylic acid via the addition funnel. The exotherm was noted and the mixture heated at 120° C. for 2 hours. Without being bound by theory, the presumed predominant intermediate and product are illustrated schematically below:

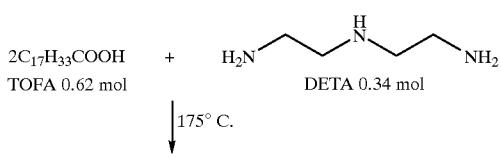

-continued

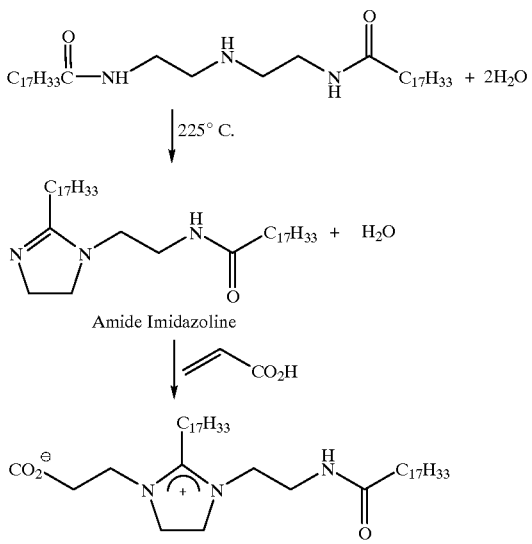

Amide Imidazoline

INHIBITOR PERFORMANCE

The performance of the inhibitor produced in the Example was evaluated by Wheelbox, Stirred Kettle and Flow Loop Tests. Each of the tests is described below and the results of the three tests are presented in tabular form.

Wheelbox Test

The Wheelbox Tests were conducted at 80° C. in a rotary oven. The coupons used were flat rectangular carbon steel coupons which had been water quenched and hardened. To prepare the coupons, metal surfaces were sand blasted, washed in an alcohol/toluene mixture and dried. The prepared coupons were weighed and placed individually in sample bottles.

The test medium was 90% by volume of a seawater brine and 10% by volume of kerosene. The fluid was sparged with $CO_2$. Each bottle was dosed with a measured amount of the inhibitor to be tested (2, 5 or 10 ppm in Wheelbox Test A and 5, 7.5 and 10 ppm in Wheelbox Tests B, C and D). Finally, the coupons were placed in the bottles which were then capped and shaken.

The oven was heated to 80° C. and loaded with the coupon-containing bottles. The bottles were rotated in the oven for a period of 24 hours. After cleaning and drying, the coupons were reweighed and the percent corrosion inhibition was calculated using the formula:

$$\frac{\text{average blank weight loss} - \text{weight loss of treated coupon}}{\text{average blank weight loss}} \times 100$$

Each coupon was also visually inspected and the appearance was recorded.

The inhibitor was tested in four Wheelbox Tests A–D. Wheelbox Test A was an "actives only" test. Wheelbox Tests B, C and D were tests of the inhibitor at 8, 30 and 38 wt %, respectively, in formulations typically used in commercial applications.

The results presented in Table II are for Wheelbox Test A ("actives only"). The term "actives only" means that the test was conducted with the final product of the Example only. The product was not mixed into a formulation, such as described above, typically used in commercial applications. The "actives only" test was used as a preliminary indicator of the effectiveness of the inhibitor. The control used in the "actives only" Wheelbox Test A was the product of Example I of U.S. Pat. No. 5,322.640 (i.e. an acrylated imidazoline: the imidazoline was prepared with a 1:1 mole ratio of TOFA:DETA). As discussed above, the Applicant has discovered that the method described for producing a quaternized amino imidazoline in U.S. Pat. No. 5,322,640 could produce at least some quaternized amido imidazoline as a portion of the final product mixture.

TABLE II

| | Wheelbox Test A - Actives Only | | |
| | % Protection @ | | |
| Inhibitor | 2 ppm | 5 ppm | 10 ppm |
| --- | --- | --- | --- |
| Blank | 0 | 0 | 0 |
| Control | 71 | 86 | 90 |
| Example | 62 | 85 | 90 |

Wheelbox Test A demonstrates that the inhibitor produced in the Example provided corrosion protection comparable to that of the Control inhibitor. However, as discussed above, the inhibitor produced in the Example costs significantly less to produce than the Control inhibitor.

Moreover, the comparable or improved performance results of the Example versus the Control are surprising and unexpected. The results are surprising and unexpected because the primary compound of the Example does not contain a free amine or a freely available lone pair of electrons on a heteroatom in the group pendant to the second nitrogen of the imidazoline ring. The lone pair of electrons is associated with a nitrogen adjacent to a carbonyl group. Accordingly, it was surprising and unexpected that this type of compound (a) would have any significant positive effect on inhibitor performance whatsoever and (b) would perform comparably to the Control.

The inhibitor of the Example was then tested in a corrosion inhibition formulation, as an example of a commercial application. The Control I formulation used in Wheelbox Tests B, C and D was a proprietary corrosion inhibition formulation produced by Nalco/Exxon Energy Chemicals, L.P., Sugar Land, Tex. The Control I formulation includes up to 38% of a proprietary corrosion inhibitor active.

In Wheelbox Test B, 8 wt % of the corrosion inhibitor active of the Control I inhibitor formulation was substituted with 8 wt % of the product of the Example to produce the Example formulation. In the Control II inhibitor formulation for Wheelbox Test B, 8 wt % of the corrosion inhibitor active of the Control I inhibitor formulation was substituted with 8 wt % of the product of Example I of U.S. Pat. No. 5,322,640 (i.e. an acrylated imidazoline; the imidazoline was prepared with a 1:1 mole ratio of TOFA:DETA). The amounts and type of the remaining components of the Control I inhibitor formulation were constant in all formulations. The results are shown in Table III.

TABLE III

Wheelbox Test B - 8 wt % formulation

| Inhibitor | % Protection @ | | |
|---|---|---|---|
| | 5 ppm | 7.5 ppm | 10 ppm |
| Blank | 0 | 0 | 0 |
| Control I | 63 | 66 | 78 |
| Control II | 78 | 88 | 86 |
| Example | 85 | 85 | 92 |

The formulation containing the inhibitor produced in the Example gave better corrosion protection results as compared with the Control I inhibitor formulation. The formulation containing the inhibitor produced in the Example gave comparable or better corrosion protection results as compared with the Control II inhibitor formulation. Again, for the reasons discussed above, these results are both surprising and unexpected.

In Wheelbox Test C, 30 wt % of the corrosion inhibitor active of the Control I inhibitor formulation was substituted with 30 wt % of the product of the Example to produce the Example formulation. In the Control II inhibitor formulation for Wheelbox Test C, 30 wt % of the corrosion inhibitor active of the Control I inhibitor formulation was substituted with 30 wt % of the product of Example I of U.S. Pat. No. 5,322,640 (i.e. an acrylated imidazoline; the imidazoline was prepared with a 1:1 mole ratio of TOFA:DETA). The amounts and type of the remaining components of the Control I inhibitor formulation were constant in all formulations. ThU results are shown in Table IV.

TABLE IV

Wheelbox Test C - 30 wt % formulation

| Inhibitor | % Protection @ | | |
|---|---|---|---|
| | 5 ppm | 7.5 ppm | 10 ppm |
| Blank | 0 | 0 | 0 |
| Control I | 63 | 66 | 78 |
| Control II | 89 | 93 | 97 |
| Example | 59 | 84 | 83 |

The formulation containing the inhibitor produced in the Example gave better corrosion protection results as compared with the Control I inhibitor formulation. The formulation containing the inhibitor produced in the Example gave comparable corrosion protection results as compared with the Control II inhibitor formulation. The inhibitor of the Example produced slightly lower inhibition performance at 7.5 ppm and significantly lower inhibition performance at 5 ppm. In view of the performance of the Example inhibitor at 5 ppm versus the Control II inhibitor formulation in an 8 wt % and 38 wt % active formulation (see Tables III, V, VI and VII), this result of the Example inhibitor at 5 ppm in a 30 wt % active formulation is most probably aberrational. Also, in Wheelbox Test A where actives alone were evaluated (see Table II), the Example versus the Control inhibitor (i.e., the same used in the Control II inhibitor formulation) is generally comparable. Therefore, despite this aberrational result for the Example inhibitor in this particular test, the general results of Wheelbox Test C are surprising and unexpected for the reasons stated above.

In Wheelbox Test D, 38 wt % of the corrosion inhibitor active of the Control I inhibitor formulation was substituted with 38 wt % of the product of the Example to produce the Example formulation. In the Control II inhibitor formulation for Wheelbox Test D, 38 wt % of the corrosion inhibitor active of the Control I inhibitor formulation was substituted with 38 wt % of the product of Example I of U.S. Pat. No. 5,322,640 (i.e. an acrylated imidazoline; the imidazoline was prepared with a 1:1 mole ratio of TOFA:DETA). The amounts and type of the remaining components of the Control I inhibitor formulation were constant in all formulations. The results are shown in Table V.

TABLE V

Wheelbox Test D - 38 wt % formulation

| Inhibitor | % Protection @ | | |
|---|---|---|---|
| | 5 ppm | 7.5 ppm | 10 ppm |
| Blank | 0 | 0 | 0 |
| Control I | 63 | 66 | 78 |
| Control II | 92 | 96 | 96 |
| Example | 80 | 87 | 92 |

The formulation containing the inhibitor produced in the Example gave better corrosion protection results as compared with the Control I inhibitor formulation. The formulation containing the inhibitor produced in the Example gave comparable corrosion protection results as compared with the Control II inhibitor formulation. Therefore, for the reasons stated above these results are surprising and unexpected.

Stirred Kettle Test

A "stirred kettle" apparatus was used to measure the corrosion inhibition capabilities of the corrosion inhibitors of the present invention.

The stirred kettle apparatus was a 1 L resin kettle with a four-neck removable top. A magnetic stirrer was used to agitate the fluids and a sparge tube was used to purge the fluids with $N_2$ to remove any $O_2$. A thermocouple and temperature controller were used to monitor/maintain the temperature of the system. The fluid used for the tests consisted of 700 mL brine and 300 mL kerosene. The fluid was stirred for 14 hours at 80° C.

A baseline corrosion rate was measured and the system was then dosed with the corrosion inhibitor. Corrosion rates were measured using a probe with two electrodes (reference and working). The probes were connected to a CORRATER (Rohrbach Instruments, Santa Fe Springs, Calif.), which recorded corrosion rates at periodic intervals. The CORRATER used the method of linear polarization resistance (LPR, ASTM procedure G59–91) to determine corrosion rates. The data was then downloaded to a spreadsheet software program which allowed graphical interpretation of the results.

The Control I inhibitor formulation was as described above with reference to Wheelbox Tests B, C and D. 30 wt % of the corrosion inhibitor active of the Control I inhibitor formulation was substituted with 30 wt % of the inhibitor of the Example to produce the Example formulation. The inhibitor formulation was used at a concentration of 2.5 ppm. Table VI illustrates the results of the Stirred Kettle Test.

TABLE VI

Stirred Kettle Test

| Inhibitor | (% Active Substituted)/ (% Total Active in Control I) | % Protection after 14 hours |
|---|---|---|
| Blank | 0/0 | 0 |
| Control I | 0/38 | 85 |
| Example | 30/38 | 86 |

The results of the Stirred Kettle Test show comparable corrosion inhibition by the formulation containing the inhibitor produced in the Example, as compared with the Control I inhibitor formulation. Again, this result is surprising and unexpected for the reasons discussed above.

Flow Loop Test

The inhibitor produced in the Example was also tested using a flow loop (high shear stress conditions). The flow loop was a closed loop of 1" (i.d.) 316L stainless steel tubing which held a total of 14 gallons of fluid. A high shear area was created in the loop where the inside diameter of the loop was reduced to ¼".

The fluid used was a 90:10 synthetic seawater/brine solution. The test was conducted for 16 hours at 80° C. and a $CO_2$ partial pressure of 35 psi at a fluid flow rate of 35 gal/min.

Cylindrical mild steel coupons were centered in various parts of the 1" annular flow line ("Annular Probes") and in the ¼" annular flow line ("High Shear Area"). Corrosion of mild steel coupons was measured electrochemically, using the LPR method (ASTM procedure G59–91) to determine corrosion rates. The percent protection was calculated using the formula:

$$\frac{\text{corrosion rate with no inhibitor} - \text{corrosion rate with inhibitor}}{\text{corrosion rate with no inhibitor}} \times 100$$

Control I inhibitor formulation was as described above with reference to Wheelbox Tests B, C and D. 8 wt %, 30 wt % or 38 wt % of the corrosion inhibitor active of the Control I inhibitor formulation was substituted with the inhibitor of the Example to produce the Example formulation (indicated by 8 wt %, 30 wt % or 38 wt % active, respectively). The inhibitor formulation was used at a concentration of 25 ppm in the synthetic seawater/brine solution. Table VII illustrates the results of the Flow Loop Test.

TABLE VII

Flow Loop Test

| | (% Active Substituted)/ | % Protection after 16 hours | |
|---|---|---|---|
| Inhibitor | (% Total Active in Control I) | Annular Probes | High Shear Area |
| Blank | 0/0 | 0 | 0 |
| Control I | 0/38 | 50 | 92 |
| Example | 8/38 | 44 | — |
| Example | 30/38 | 77 | 99 |
| Example | 30/38 | 76 | 99 |
| Example | 38/38 | 95 | 95 |

The Flow Loop Test results show that the formulation containing the inhibitor produced in the Example provided significantly better corrosion protection than the Control I inhibitor formulation when 38% of the corrosion inhibitor active of the Control I inhibitor formulation was substituted. Again, these results are surprising and unexpected for the reasons discussed above.

Preferred compositions and applications for practicing the invention, as well as preferred processes for making such compositions, have been described. It will be understood that the foregoing is illustrative only and that other compositions, processes for making such compositions, and applications for such compositions can be employed without departing from the true scope of the invention defined in the following claims.

What I claim is:

1. A method of using a corrosion inhibitor composition for reducing the corrosion rate of a metal by a fluid having at least one corrosion agent, said method comprising:

(a) introducing said corrosion inhibitor composition into said fluid, said inhibitor composition having at least a first compound, A, and a second compound, B, wherein the A:B mole ratio is in a range of from about 1.1:1 to about 1000: 1, wherein (i) A is a quaternized compound having the general formula:

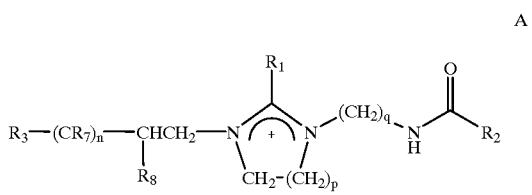

A wherein, $R_1$ and $R_2$ are each independently a moiety selected from the group consisting of:
   (i) substituted and unsubstituted, saturated and unsaturated alkyl groups having from about 5 to about 29 carbon atoms;
   (ii) substituted and unsubstituted, saturated and unsaturated alkyl groups having from about 5 to about 29 carbon atoms, wherein said alkyl group is at least oxygenized, sulfurized or phosphorylized; and
   (iii) combinations thereof;

$R_3$ is a moiety selected from the group consisting of —$CO_2H$, —$SO_3H$, —$PO_3H_2$, —$CO_2R_7$, —$CONH_2$, —$CONHR_7$ and —$CON(R_7)_2$ groups and combinations thereof;

each $R_7$ is independently selected from the group consisting of hydrogen and linear and branched alkyl, aryl, alkylaryl, cycloalkyl and heteroaromatic groups having from 1 to about 10 carbon atoms, and combinations thereof;

$R_8$ is hydrogen or a linear alkyl group having from 1 to about 10 carbon atoms; and n=0 to about 8, p=1 to about 5 and q=2 to about 10; and (ii) B is a quaternized compound having the general formula:

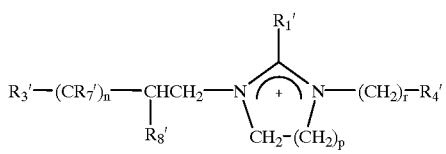

wherein,
R$_1$' is a moiety selected from the group consisting of:
(i) substituted and unsubstituted, saturated and unsaturated alkyl groups having from about 5 to about 29 carbon atoms;
(ii) substituted and unsubstituted, saturated and unsaturated alkyl groups having from about 5 to about 29 carbon atoms, wherein said alkyl group is at least oxygenized, sulfurized or phosphorylized; and
(iii) combinations thereof;
R$_4$' is a moiety selected from the group consisting of polyalkylene polyamines, alcohol and thiol groups having from about 2 to about 16 carbon atoms, and combinations thereof;
R$_3$' is a moiety selected from the group consisting of —CO$_2$H, —SO$_3$H, —PO$_3$H$_2$, —CO$_2$R$_7$', —CONH$_2$, —CONHR$_7$' and —CON(R$_7$')$_2$ groups and combinations thereof;
each R$_7$' is independently selected from the group consisting of hydrogen and linear and branched alkyl, aryl, alkylaryl, cycloalkyl and heteroaromatic groups having from 1 to about 10 carbon atoms, and combinations thereof;
R$_8$' is hydrogen or a linear alkyl group having from 1 to about 10 carbon atoms; and
n=0 to about 8, p=1 to about 5 and r=0 to about 10; and
(b) contacting said metal with the fluid of step (a).

2. The method of claim 1 wherein R$_1$, of said compound A is selected from the group consisting of (a) unsubstituted, unsaturated alkyl groups having from about 7 to about 23 carbon atoms, (b) substituted, unsaturated alkyl groups having from about 7 to about 23 carbon atoms, and (c) sulfurized unsubstituted, saturated and unsaturated alkyl groups having from about 7 to about 23 carbon atoms.

3. The method of claim 1 wherein R$_2$ of said compound A is selected from the group consisting of (a) unsubstituted, unsaturated alkyl groups having from about 7 to about 23 carbon atoms, (b) substituted, unsaturated alkyl groups having from about 7 to about 23 carbon atoms, and (c) sulfurized unsubstituted, saturated and unsaturated alkyl groups having from about 7 to about 23 carbon atoms.

4. The method of claim 1 wherein R$_3$ of said compound A is a carboxylate moiety.

5. The method of claim 1 wherein R$_4$' of said compound B has the general formula:

wherein, X is selected from the group consisting of NH$_2$, NHR$_6$, N(R$_6$)$_2$, OH and SH, and combinations thereof, each R$_6$ is independently a linear alkyl group or branched alkyl group having from 1 to about 8 carbon atoms, and m=0 to about 5.

6. A method of using a corrosion inhibitor composition for reducing the corrosion rate of a metal by a fluid having at least one corrosion agent, said method comprising:

(a) introducing said corrosion inhibitor composition into said fluid, said inhibitor composition having at least a first compound, A, and being substantially free of a second compound, B, wherein
(i) A is a quaternized amido compound having the general formula:

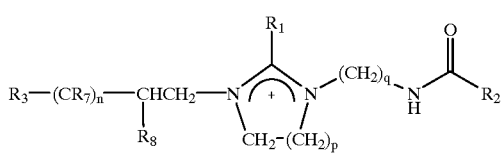

wherein,
R$_1$ and R$_2$ are each independently a moiety selected from the group consisting of:
(i) substituted and unsubstituted, saturated and unsaturated alkyl groups having from about 5 to about 29 carbon atoms;
(ii) substituted and unsubstituted, saturated and unsaturated alkyl groups having from about 5 to about 29 carbon atoms, wherein said alkyl group is at least oxygenized, sulfurized or phosphorylized; and
(iii) combinations thereof;
R$_3$ is a moiety selected from the group consisting of —CO$_2$H, —SO$_3$H, —PO$_3$H$_2$, —CO$_2$R$_7$, —CONH$_2$, —CONHR$_7$ and —CON(R$_7$)$_2$ groups and combinations thereof;
each R$_7$ is independently selected from the group consisting of hydrogen and linear and branched alkyl, aryl, alkylaryl, cycloalkyl and heteroaromatic groups having from 1 to about 10 carbon atoms, and combinations thereof;
R$_8$ is hydrogen or a linear alkyl group having from 1 to about 10 carbon atoms; and
n=0 to about 8, p=1 to about 5 and q=2 to about 10; and
(ii) B is a quaternized compound having the general formula:

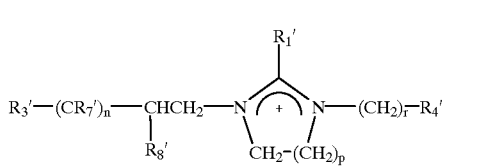

wherein,
R$_1$' is a moiety selected from the group consisting of:
(i) substituted and unsubstituted, saturated and unsaturated alkyl groups having from about 5 to about 29 carbon atoms;
(ii) substituted and unsubstituted, saturated and unsaturated alkyl groups having from about 5 to about 29 carbon atoms, wherein said alkyl group is at least oxygenized, sulfurized or phosphorylized; and
(iii) combinations thereof;
R$_4$' is a moiety selected from the group consisting of polyalkylene polyamine groups having from about 2 to about 16 carbon atoms, and combinations thereof;
R$_3$' is a moiety selected from the group consisting of —CO$_2$H, —SO$_3$H, —PO$_3$H$_2$, —CO$_2$R$_7$', —CONH$_2$, —CONHR$_7$' and —CON(R$_7$')$_2$ groups and combinations thereof;

each $R_7'$ is independently selected from the group consisting of hydrogen and linear and branched alkyl, aryl, alkylaryl, cycloalkyl and heteroaromatic groups having from 1 to about 10 carbon atoms, and combinations thereof;

$R_8'$ is hydrogen or a linear alkyl group having from 1 to about 10 carbon atoms; and n=0 to about 8, p=1 to about 5 and r=0 to about 10; and (b) contacting said metal with the fluid of step (a).

7. The method of claim 6 wherein $R_1$ of said compound A is selected from the group consisting of (a) unsubstituted, unsaturated alkyl groups having from about 7 to about 23 carbon atoms, (b) substituted, unsaturated alkyl groups having from about 7 to about 23 carbon atoms, and (c) sulfurized unsubstituted, saturated and unsaturated alkyl groups having from about 7 to about 23 carbon atoms.

8. The method of claim 6 wherein $R_2$ of said compound A is selected from the group consisting of (a) unsubstituted, unsaturated alkyl groups having from about 7 to about 23 carbon atoms, (b) substituted, unsaturated alkyl groups having from about 7 to about 23 carbon atoms, and (c) sulfurized unsubstituted, saturated and unsaturated alkyl groups having from about 7 to about 23 carbon atoms.

9. The method of claim 6 wherein $R_3$ of said compound A is a carboxylate moiety.

10. A process for producing a composition comprising at least a quaternized compound having an amido moiety, comprising the steps of:

(a) selecting a first organic compound from the group consisting of:
(i) substituted and unsubstituted, saturated and unsaturated fatty acids having from about 6 to about 30 carbon atoms;
(ii) substituted and unsubstituted, saturated and unsaturated fatty acids having from about 6 to about 30 carbon atoms, wherein said fatty acid is at least oxygenized, sulfurized or phosphorylized; and
(iii) combinations thereof;

(b) selecting an alkyl polyamine from the group having the general formula:

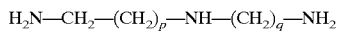

wherein p=1 to about 5 and q=2 to about 10;

(c) selecting a second organic compound from the group consisting of:
(i) substituted and unsubstituted, α,β-unsaturated carboxylic fatty acids, and amide and ester derivatives thereof, having from about 3 to about 11 carbon atoms;
(ii) substituted and unsubstituted, α,β-unsaturated sulfonic and phosphonic fatty acids having from about 2 to about 11 carbon atoms; and
(iii) combinations thereof;

(d) mixing said first organic compound and said alkyl polyamine in a mole ratio in a range of from about 1.1:1 to about 500:1 to produce at least one intermediate compound, wherein said mole ratio is the total moles of said first organic compound to the total moles of said alkyl polyamine, and (e) mixing said at least one intermediate compound with said second organic compound to produce said composition.

11. The process of claim 10 wherein the quaternized compound having an amido moiety has the general formula:

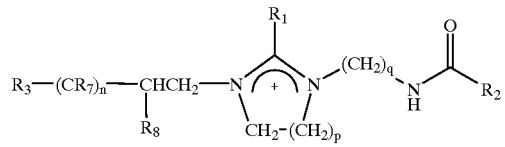

wherein
$R_1$ and $R_2$ are each independently a moiety selected from the group consisting of:
(i) substituted and unsubstituted, saturated and unsaturated alkyl groups having from about 5 to about 29 carbon atoms;
(ii) substituted and unsubstituted, saturated and unsaturated alkyl groups having from about 5 to about 29 carbon atoms, wherein said alkyl group is at least oxygenized, sulfurized or phosphorylized; and
(iii) combinations thereof;
$R_3$ is a moiety selected from the group consisting of $-CO_2H$, $-SO_3H$, $-PO_3H_2$, $-CO_2R_7$, $-CONH_2$, $-CONHR_7$ and $-CON(R_7)_2$ groups and combinations thereof;
each $R_7$ is independently selected from the group consisting of hydrogen and linear and branched alkyl, aryl, alkylaryl, cycloalkyl and heteroaromatic groups having from 1 to about 10 carbon atoms, and combinations thereof;
$R_8$ is hydrogen or a linear alkyl group having from 1 to about 10 carbon atoms; and
n=0 to about 8, p=1 to about 5 and q=2 to about 10.

12. The process of claim 10 wherein said at least one intermediate compound has the general formula:

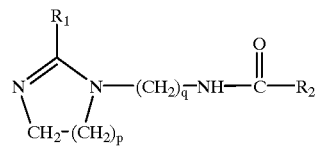

wherein
$R_1$ and $R_2$ are each independently a moiety selected from the group consisting of:
(i) substituted and unsubstituted, saturated and unsaturated alkyl groups having from about 5 to about 29 carbon atoms;
(ii) substituted and unsubstituted, saturated and unsaturated alkyl groups having from about 5 to about 29 carbon atoms, wherein said alkyl group is at least oxygenized, sulfurized or phosphorylized; and
(iii) combinations thereof;
p=1 to about 5 and q=2 to about 10.

13. The process of claim 11 wherein $R_1$ of said quaternized compound is selected from the group consisting of (a) unsubstituted, unsaturated alkyl groups having from about 7 to about 23 carbon atoms, (b) substituted, unsaturated alkyl groups having from about 7 to about 23 carbon atoms, and (c) sulfurized unsubstituted, saturated and unsaturated alkyl groups having from about 7 to about 23 carbon atoms.

14. The process of claim 11 wherein $R_2$ of said quaternized compound is selected from the group consisting of (a)

unsubstituted, unsaturated alkyl groups having from about 7 to about 23 carbon atoms, (b) substituted, unsaturated alkyl groups having from about 7 to about 23 carbon atoms, and (c) sulfurized unsubstituted, saturated and unsaturated alkyl groups having from about 7 to about 23 carbon atoms.

15. The process of claim 11 wherein $R_3$ of said quaternized compound is a carboxylate moiety.

16. The composition produced by the process of claim 10.

17. A method of using the composition produced by the process of claim 10 for reducing the corrosion rate of a metal by a fluid having at least one corrosion agent, said method comprising:

(a) introducing said composition into said fluid; and (b) contacting said metal with the fluid of step (a).

* * * * *